United States Patent [19]

Hemker

[11] 4,454,113

[45] Jun. 12, 1984

[54] STABILIZATION OF OIL AND WATER EMULSIONS USING POLYGLYCEROL ESTERS OF FATTY ACIDS

[75] Inventor: Wilfred J. Hemker, Berea, Ohio

[73] Assignee: SCM Corporation, New York, N.Y.

[21] Appl. No.: 420,768

[22] Filed: Sep. 21, 1982

[51] Int. Cl.$^3$ .............. B01J 13/00; A01N 61/02; A61K 31/00; A61K 47/00

[52] U.S. Cl. .................. 424/63; 252/312; 424/172; 424/365

[58] Field of Search ............. 252/312; 424/172, 63, 424/365

[56] References Cited

U.S. PATENT DOCUMENTS

| | | | |
|---|---|---|---|
| 2,965,493 | 12/1960 | Mancuso et al. | 99/139 |
| 3,170,836 | 2/1965 | Vergine | 424/172 |
| 3,341,465 | 9/1967 | Kaufman et al. | 252/316 |
| 3,359,116 | 12/1967 | Little et al. | 99/54 |
| 3,370,955 | 2/1968 | Little | 99/54 |
| 3,391,002 | 7/1968 | Little | 99/54 |
| 3,433,643 | 3/1969 | Tatter et al. | 99/59 |
| 3,437,494 | 4/1969 | Loter et al. | 99/144 |
| 3,514,298 | 5/1970 | Noznick et al. | 99/123 |
| 3,803,333 | 4/1974 | Roudebush | 426/163 |
| 3,843,815 | 10/1974 | Reesman | 99/214 |
| 3,889,005 | 6/1975 | Brammer et al. | 426/585 |
| 3,936,391 | 2/1976 | Gabby et al. | 252/356 |
| 3,946,122 | 3/1976 | Scharp | 426/604 |
| 3,954,658 | 5/1976 | Tsutsumi et al. | 252/312 |
| 3,958,033 | 5/1976 | Sima | 426/602 |
| 3,966,632 | 6/1976 | Colliopoulos et al. | 252/309 |
| 3,996,390 | 12/1976 | Igoe | 426/573 |
| 4,058,636 | 11/1977 | Igoe | 426/573 |
| 4,061,684 | 12/1977 | Helfert et al. | 260/615 B |
| 4,164,564 | 8/1979 | Chen | 424/172 |
| 4,226,890 | 10/1980 | Howard | 426/92 |
| 4,335,103 | 6/1982 | Barker et al. | 424/59 |
| 4,350,605 | 9/1982 | Hughett | 252/305 |

FOREIGN PATENT DOCUMENTS

919498  1/1973  Canada .................. 99/143

OTHER PUBLICATIONS

Journal of the Society of Cosmetics Chemistry, J. Soc. Cos. Chem. 15, 473-483 (1964).

*Primary Examiner*—Richard D. Lovering
*Assistant Examiner*—Catherine S. Kilby
*Attorney, Agent, or Firm*—Richard H. Thomas

[57] ABSTRACT

A process for the preparation of smooth oil and water emulsions of excellent texture and appearance comprising adding together emulsion-forming ingredients consisting essentially of oil, water, and surfactant; selecting as said surfactant a polyglycerol ester of a fatty acid having a fatty acid composition which is primarily palmitic and stearic acids, said ester having an average degree of polymerization in the range of about 2 to about 6, a hydroxyl number in the range of about 280-425, and a saponification number in the range of about 120-140; and intensively mixing said ingredients together at an elevated temperature; said mixing being carried out at a pH greater than about 7.0.

In a preferred embodiment, the pH subsequent to mixing is reduced to about 5-7.5, to produce a gelled emulsion having the texture and appearance of oil-rich emulsions, the proportions of oil and surfactant of the gelled emulsion being about 5-25% and 2.5-10%, respectively, based on the weight of gel-forming ingredients.

The present invention also relates to emulsions prepared by the processes herein and to products containing active ingredients in addition to the emulsion-forming ingredients.

15 Claims, No Drawings

STABILIZATION OF OIL AND WATER EMULSIONS USING POLYGLYCEROL ESTERS OF FATTY ACIDS

TECHNICAL FIELD

The subject matter of the present application is related to that of co-pending application Ser. No. 257,983, filed Apr. 27, 1981, assigned to assignee of the present application.

The present invention relates to a method for the production of oil and water emulsions broadly, and, in a preferred embodiment, to the production of oil and water gelled emulsions of low fat content which have a creamy gelled consistency characteristic of conventional emulsions of much higher fat content.

The present invention is particularly useful for the preparation of cosmetics and lotions, although it will be apparent to those skilled in the art that it has other applications, for instance in the food or pharmaceutical industry or the preparation of shaving creams.

The present invention also relates to emulsions prepared by the methods hereof, and to products containing such emulsions.

For purposes of the present application, the term "oil" means either a fat of vegetable, animal, or petroleum origin which is normally plastic at room temperature, or an oil of similar origin which is normally fluid at room temperature. The term "oil-in-water emulsions" denotes emulsions prepared using the fats as above defined, wherein the oil ingredient is dispersed within a continuous phase of water.

BACKGROUND ART

Emulsions of oil and water usually are prepared with the add of a surfactant of some sort. The oil and surfactant, if the surfactant is a lipid, are heated to an elevated temperature sufficient to liquify these components, and they are then mixed with the water, also at an elevated temperature, under high agitation and shear conditions, for instance by homogenization, sufficient to form the emulsion. Depending upon the relative concentrations of the several components, either water or oil may be the continuous phase.

Usually, the better cosmetic or lotion emulsions have a high oil content, for instance more than 50% on a weight basis, so that oil is the continuous phase. The emulsions are characteristically smooth, homogeneous, and creamy in texture. In the case of oil-in-water emulsions, where water is the continuous phase, these tend to be more difficult to stabilize against phase separation, and stability often is obtained only with the assistance of a hydrocolloid such as a protein or gum. Protein, for instance, behaves as a film former around the emulsified fat globule, stabilizing the emulsion.

It is known that with certain surfactants, the pH of the emulsion can have a decided effect on the characteristics of the emulsion. This has been observed, for instance, with the use of distilled monoglycerides, wherein an acidic condition seems to give a firmer gel structure having a higher degree of rigidity, more so than one would expect from the proportions of ingredients present.

The present invention is based on the discovery that the properties of an emulsion, where the surfactant is a particular class of polyglycerol esters of fatty acids, can also be carefully controlled by controlling the emulsion pH.

The present invention with regard to the preferred embodiment hereof, particularly is based on the discovery of a critical pH window in which a firm gel can be formed using a lower proportion of lipids than would normally be used to form an emulsion of the same degree of firmness.

A feature of the present invention is that the emulsions are formed and are stable without the use of a hydrocolloid, such as a gum or protein, conventionally employed for stabilization of emulsions.

DISCLOSURE OF INVENTION

In accordance with the concepts of the present invention, improved smooth water and oil emulsions having an excellent texture and appearance are obtained by including in such emulsions a polyglycerol ester of a fatty acid characterized as having an average degree of polymerization of about 2-6, a hydroxyl number in the range of about 280 to about 425, and a saponification number in the range of about 120 to about 140, said polyglycerol ester having a fatty acid composition which is primarily palmitic and stearic acids; and intensively mixing said emulsions at a pH greater than about 7, the proportions of oil and plyglycerol ester preferably being in the ranges of about 5-25% and about 2.5-10%, respectively, based on the total weight of the emulsion-forming ingredients. A characteristic of the emulsions hereof is that they have an average particle size less than about ten microns.

A preferred polyglycerol ester useful in the emulsions of the present invention is triglycerol monostearate.

In a preferred embodiment, the pH subsequent to mixing is reduced to about 5-7.5 to produce gelled emulsions having the texture and appearance of conventional lipid emulsions of much greater oil content.

The present invention also resides in the emulsions made by the methods herein, and also to products containing such emulsions and having active pharmaceutical or cosmetic ingredients, in addition to the emulsion-forming ingredients.

BEST MODE FOR CARRYING OUT THE INVENTION AND INDUSTRIAL APPLICABILITY

The emulsions of the present invention are either fluid or gelled depending upon the pH of the emulsion-forming ingredients. Initially, intensive mixing is carried out at a pH greater than about 7, obtained by adding to the emulsion a moderately weak or dilute base or alkalizing agent such as sodium carbonate, sodium stearate, or dilute sodium hydroxide. This gives a product which is fluid in nature but very smooth, having a fine particle size less than about ten microns. The emulsions are very stable and resistant to freeze-thaw cycling. (Note 1)

Subsequently, the pH may, if desired, be lowered to a range of about 5-7.5 by the addition of a moderately weak acid such as citric, or dilute hydrochloric acid. This produces a firm, gelled structure having the texture and appearance of conventional lipid emulsions of much greater oil content. The particle size of the gelled emulsions remains at less than about ten microns. The viscosity, depending upon the proportions of ingredients, is in the range of about 1,500 to 100,000 centipoises.

The phenomena of this invention, as above observed, are believed to be unique with emulsions containing the stated proportions of oil and surfactant, the surfactant being a polyglycerol ester of a fatty acid as herein defined.

The particular fat or oil employed in the process and compositions of the present invention is not critical. Preferably, it has a melting point which is not substantially higher than body temperature, and should have good flavor stability and bland flavor. A number of hydrogenated cottonseed and soybean oils have been found to be satisfactory. The oil can also be an animal fat or oil, or fish oil, or of petroleum origin and may or may not be suitable for human consumption, depending upon allication.

One particular oil employed in the process and composition of the present invention is a partially hydrogenated soybean or cottonseed vegetable oil, in liquid form, marketed by SCM Corporation under the trademark "Durkex 500". This fat has a Wiley Melting Point of about 73° F. max., and AOM stability of 350 hours minimum, and a free fatty acid content of about 0.05% maximum. It is hydrogenated to an IV of about 74–81, and has a SFI at 50° F. of about 14–20 and 70° F. of 3 maximum.

The fat or oil of the compositions of the present invention can be hard fat (which is normally solid at room temperature), such as "Kaomel", (trademark SCM Corporation). This hard fat, also known as a hard butter, is prepared from a blend of cottonseed and soybean oils and has a Wiley Melting Point in the range of about 97° F. to about 101° F. It is a fractionated, hydrogenated vegetable oil, and has an approximate SFI as shown in the following table.

TABLE I

| Temperature °F. | Approx. SFI Index |
| --- | --- |
| 50 | 72 |
| 70 | 63 |
| 80 | 55 |
| 92 | 25 |
| 100 | 5 max. |
| 110 | 0 |

The polyglycerol esters of the present invention are prepared by polymerizing glycerol and esterifying the polymerized glycerol products with fatty acids or glycerides, either in a direct esterification process or by interesterification, to form the polyglycerol ester product. The fatty acid composition of the polyglycerol ester should be primarily palmitic or stearic acid. The polyglycerols useful in the present invention contain about 2 to about 6 units of glycerol and 1 to about 2 saturated or unsaturated fatty acid groups per molecule. They have an approximate ester hydroxyl number in the range of about 280–425 and a saponification number in the range of about 120–140, and are prepared using 0-5 IV stearine or by esterification with a fully saturated fatty acid.

A representative fatty acid ester of polyglycerol is triglycerol monostearate, marketed by SMC Corporation under the trademark "Santone 3-1-S". The average degree of polymerization of this compound is 3. It has an approximate ester hydroxyl number of about 360.

The fat or oil, polyglycerol ester, and water, are the essential emulsion forming ingredients of the present invention. In addition to these ingredients, products of the present invention can have so-called active ingredients for cosmetics, lotions or pharmaceuticals, such as pigments, emollients, and the like.

The percentages of emulsion forming ingredients are about 5–25% oil and 2.5–10% polyglycerol ester, the balance being water. With these percentages of ingredients, it was found that a very thick, smooth, paste-like cream, or gelled emulsion, could be formed, the latter having the texture and appearance of emulsions obtained conventionally only with much larger amounts of fat or oil. The latter emulsions were barely pourable, or not pourable at all. Below about 5% oil, such emulsions were too thin. Above about 25% oil, the amount of oil seemed to block the gelling activity.

Preparation of the emulsions of the present invention follows generally standard or conventional techniques for forming such emulsions. Initially, the lipid ingredients are heated to an elevated temperature at which they are all molten, or fluid, and then are blended with water heated to the same temperature. Subsequently, the ingredients are mixed with high-shear agitation, for instance by homogenization, to reduce the particle size of the oil or fat droplets to less than about ten microns average particle size.

To prepare a fine particle size, smooth, fluid emulsion, a critical aspect of the present invention is carrying out the intensive mixing at a pH above about 7.0, preferably above about 7.5. Preferred proportions of ingredients are as stated. Although not to be bound by or limited to any theory, it is believed that this adjustment of pH results in the formation of an amount of soap which complements the emulsion-forming activity of the surfactant, similar possibly to the activity that may be experienced with combinations or blends of hydrophilic and hydrophobic emulsifiers. Conventionally, the pH of polyglycerol ester-containing emulsions is much lower than 7.0, for instance about 4.5–5.5.

Then, to obtain the gelled emulsions of the present invention, a critical aspect is adjusting the pH subsequent to homogenization or mixing, to one in the range of about 5 to about 7.5. Again, although not limited to or bound by any theory, it is believed that this adjustment to lower pH results in a particle contraction, agglomeration, or congealing that in turn results in the formation of a strong gel, mimicking the appearance of gels of much higher fat content, for instance 40–60% fat (characteristic of facial creams and the like).

Polyglycerol esters, by the way they are made, conventionally have an amount of soap present, along with amounts of free fatty acid. However, the amounts of soap that are conventionally present are believed to be below that obtained with pH adjustment to a range above 7. By way of example, a conventional polyglycerol ester may have about 0.3–0.6% soap (based on the weight of the polyglycerol ester composition). At this level of soap, with the fat and polyglycerol ester amounts employed in the ranges above specified, a slightly curdy composition seems to be obtained following homogenization. Also, emulsions initially formed, at low pH, although stable, tended to be coarse in texture with an average particle size up to thirty microns, and even higher. These were not characteristic of high-quality, high-fat cosmetics and lotions on the market today. At pH's above about 7, not only do the emulsions become fluid but the particle size can be dramatically reduced with intensive mixing.

In the process of the present invention, the intensive mixing should be such as to produce a particle size less than about ten microns. A conventional technique is homogenization. Other techniques are known to those skilled in the art.

The viscosity of the gelled emulsions of the present invention are within the range of about 1500 cps to about 100,000 cps, as determined on the Brookfield Viscometer, Model RVT, using a Brookfield Helipath Stand (Model C) and Bars TA to TF.

EXAMPLE

In this Example, emulsions having various levels of fat or oil and polyglycerol ester (3-1-S) were formed. The fats selected were winterized soybean oil (Durkex 500) and "Kaomel". The fat or oil content was varied from about 2.5% to 95%, and the surfactant content from about 0.5% to about 40%, based on the emulsion weight (the balance being water). At low pH, about 4.9 to 5.5, and at levels of polyglycerol ester above about 7.5, stable emulsions in terms of freeze-thaw stability could not be obtained independent of oil type or concentration. Emulsions containing less than about 7.5% polyglycerol ester formed homogeneous freeze/thaw stable emulsions. However, except at low concentrations of oil, the average particle sizes in the emulsion were above about 10 microns, e.g., 30 microns or higher. Most emulsions exhibited a curdy appearance. This was true both before and after freeze-thaw cycling, and even with homogenization of all samples.

All emulsions were then treated with amounts of sodium carbonate and sodium stearate sufficient to increase pH to various levels, followed by homogenization. Addition of sodium carbonate or sodium stearate raised to pH to about 8.5 to about 9. This addition benefitted the surfactant emulsification activity. Homogenization produced fluid, homogeneous, creamy emulsions of very fine particle size, less than ten microns and, in most, less than five microns. The emulsions were of low viscosity and had good freeze-thaw stability.

Following reacidification of the emulsions to a pH in the range of about 5 to about 7.5, with those emulsions containing about 2.5-10% polyglycerol ester and about 10% to about 25% oil or fat, thick cream gels were obtained having the appearance and texture of conventional gels of much higher fat content. Particle size was less than about 5 microns. This was possible with both oil and fat (Durkex 500 and Kaomel) emulsions. The stability of the gels was not affected by freeze-thaw cycling.

These emulsions with about 12.5% to about 35% lipid were of the oil-in-water type.

To prepare cosmetics, lotions, or other commercial products, the so-called active ingredients may be added initially with the emulsion-forming ingredients, particularly in the case of oil soluble active ingredients, although the concepts of the present invention do not preclude addition even subsequent to gel formation, for instance of water dispersible active ingredients, with mild agitation.

Note 1: This aspect of the present invention was observed broadly with emulsions varying in composition from as little as 2.5% oil or fat to as much as about 95% of this component, and from as little as 0.5% polyglycerol ester to as much as about 40% of the ester (the balance being water).

I claim:

1. A process for the preparation of oil and water emulsion gels having a firm texture and appearance of oil-rich emulsions, wherein the gel-forming ingredients consist essentially of oil, water, and surfactant, comprising the steps of;
   (a) selecting as said surfactant a polyglycerol ester of a fatty acid having a fatty acid composition which is primarily palmitic and stearic acids, said ester having an average degree of polymerization in the range of about 2 to about 6, a hydroxyl number in the range of about 280–425, and a saponification number in the range of about 120–140;
   (b) intensively mixing said ingredients together at an elevated temperature, said mixing being carried out in th presence of an effective amount of a dilute base or alkalizing agent sufficient to establish a pH greater than about 7.0; said mixing producing a smooth, stable, fluid emulsion of fine particle size;
   (c) then acidifying the emulsion of step (b) to a lower pH in the range of about 5 to 7.5 to form said gel.

2. The process of claim 1 wherein the emulsion contains active ingredients in addition to the gel-forming ingredients.

3. The process of claim 1 wherein the gelled emulsion of step (c) has a viscosity in the range of about 1,500 to 100,000 centipoises.

4. The process of claim 1 wherein the mixing of step (b) is effective to produce an emulsion having an average particle size less than about ten microns.

5. The process of claim 1 wherein the gelled emulsion contains active ingredients in addition to the gel-forming ingredients, the emulsion having a viscosity in the range of about 1,500 to 100,000 centipoises and an average particle size less than about ten microns.

6. A gelled emulsion prepared by any of the methods of claims 1, 2, 3, 4, or 5.

7. A cosmetic prepared by any of the methods of claims 1, 2, 3, 4, or 5.

8. A lotion prepared by any of the methods of claims 1, 2, 3, 4, or 5.

9. The process of claims 1, 2, 3, 4, or 5, wherein the emulsion is essentially free of any hydrocolloid.

10. An oil and water gelled emulsion, having a firm texture and appearance of an oil-rich emulsion, wherein the gel-forming ingredients consist essentially of oil, surfactant, and water, the proportions of oil and surfactant being in the ranges of about 5–25% and 2.5–10%, respectively, based on the total weight of the gel-forming ingredients, said surfactant being a polyglycerol ester of a fatty acid having an average degree of polymerization of about 2–6, a hydroxyl number in the range of about 280–425, a saponification number in the range of about 120–140, and a fatty acid composition which is primarily palmitic and stearic acids, the emulsion having a pH in the range of about 5 to 7.5, and a particle size less than about 10 microns.

11. The emulsion of claim 10 having a viscosity in the range of about 1,500 to 100,000 centipoises.

12. The gelled emulsion of claims 10 or 11 prepared by initially forming the emulsion at an elevated pH more than about 7, with intensive mixing, and then reducing the pH to the range of about 5 to 7.5.

13. The emulsion of claims 10 or 11 substantially free of any hydrocolloid.

14. A cosmetic containing the emulsion of claims 10 or 11 and cosmetic active ingredients.

15. A lotion containing the gelled emulsion of claims 10 or 11 and lotion active ingredients.

* * * * *